(12) United States Patent
Tsimbler

(10) Patent No.: US 9,585,794 B2
(45) Date of Patent: Mar. 7, 2017

(54) BABY COMPRESS

(71) Applicant: Batsheva Tsimbler, Yokneam Ilit (IL)

(72) Inventor: Batsheva Tsimbler, Yokneam Ilit (IL)

( * ) Notice: Subject to any disclaimer, the term of this patent is extended or adjusted under 35 U.S.C. 154(b) by 164 days.

(21) Appl. No.: 14/266,849

(22) Filed: May 1, 2014

(65) Prior Publication Data

US 2015/0238351 A1 Aug. 27, 2015

(51) Int. Cl.
*A61F 7/02* (2006.01)
*A61F 13/14* (2006.01)

(52) U.S. Cl.
CPC ..... *A61F 13/148* (2013.01); *A61M 2202/048* (2013.01); *A61M 2202/0484* (2013.01); *A61M 2240/00* (2013.01)

(58) Field of Classification Search
CPC ............... A61F 7/02; A61F 2007/0228; A61F 2007/0225; A61F 2007/0022
See application file for complete search history.

(56) References Cited

U.S. PATENT DOCUMENTS

| | | |
|---|---|---|
| 3,175,558 A | 3/1965 | Caillouette et al. |
| 3,889,684 A | 6/1975 | Lebold |
| 4,326,533 A | 4/1982 | Henderson |
| 4,397,315 A | 8/1983 | Patel |
| 4,645,498 A | 2/1987 | Kosak |
| 4,805,619 A | 2/1989 | Swearingen |
| 5,423,875 A | 6/1995 | Kehe |
| 5,518,009 A * | 5/1996 | Ruiz-Gonzalez ....... A61F 5/028 128/869 |
| 6,070,585 A * | 6/2000 | Fery ........................ A47D 13/08 128/845 |
| 6,786,880 B2 | 9/2004 | Wall |
| 2004/0158217 A1* | 8/2004 | Wu ............................ B05C 3/12 604/385.01 |
| 2007/0106356 A1* | 5/2007 | Carstens .............. A41D 13/005 607/112 |
| 2008/0058701 A1* | 3/2008 | Smith ................... A61K 9/0009 604/20 |
| 2008/0108986 A1* | 5/2008 | Meneses .................... A61F 7/02 606/28 |
| 2009/0025735 A1* | 1/2009 | Lavigne .................... A61F 5/03 128/876 |

FOREIGN PATENT DOCUMENTS

EP 0691111 3/1996

OTHER PUBLICATIONS

NEXCARE™ ColdHot Back & Abdomen Gel Pack Belt, by 3M.
Comfort Wrap lower back and tummy heat pack belt from Saje Products.

* cited by examiner

*Primary Examiner* — Susan Su
(74) *Attorney, Agent, or Firm* — Avery N. Goldstein; Blue Filament Law PLLC

(57) ABSTRACT

A baby compress including: a strip sized to be wrapped around the abdomen of a baby; a pocket on said strip adapted to hold a liquid-soaked wipe, wherein the pocket has: an inner wall facing the baby and comprising mesh adapted to allow the liquid to permeate there through; and a back wall lined with impervious retention layer, adapted to reduce evaporation and leakage of the liquid through the back wall of the pocket; and a fastener for fastening said strip while it is wrapped around the abdomen of a baby.

12 Claims, 6 Drawing Sheets

BABY COMPRESS

Figure 1:
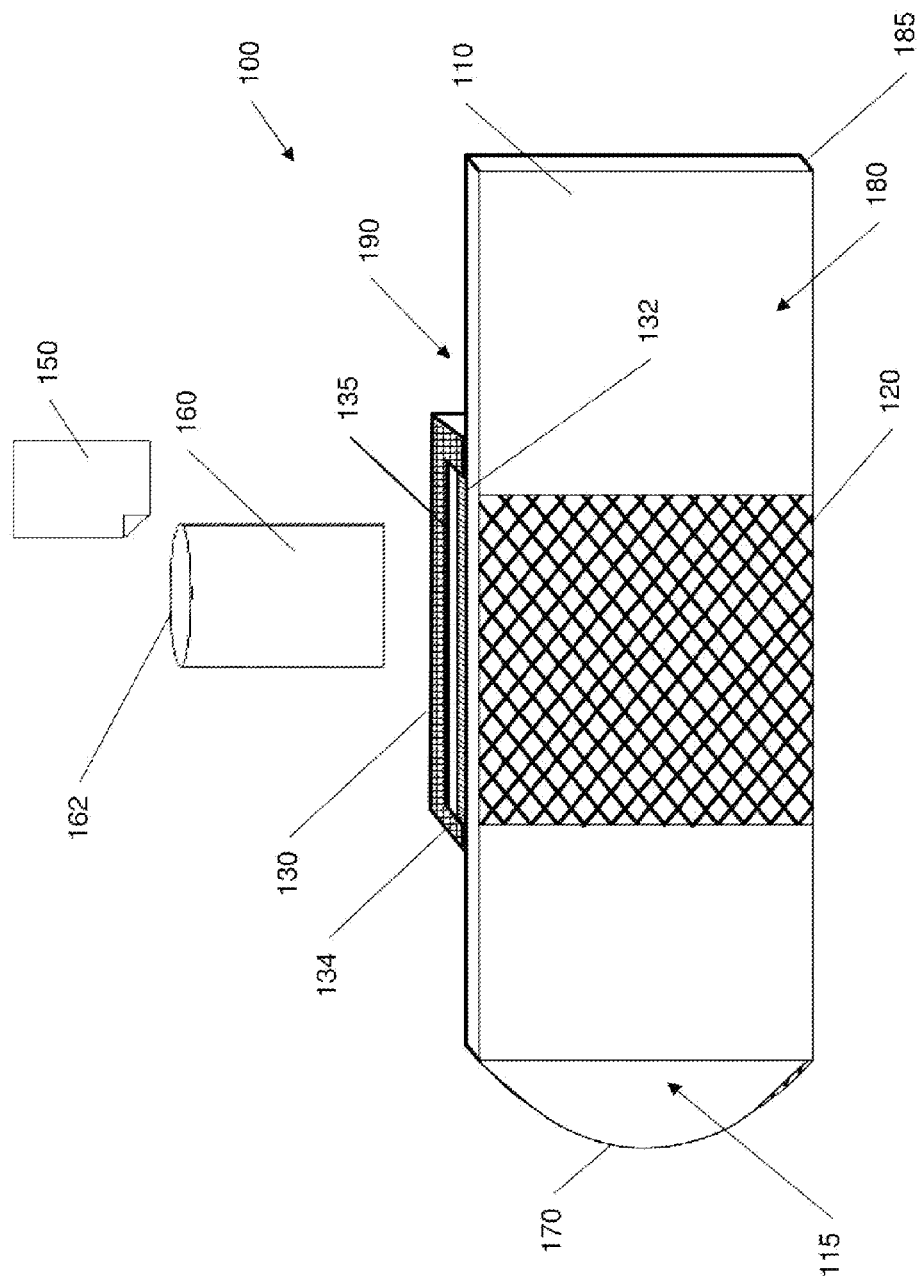

This application claims priority under 35 U.S.C. §119 (a) from IL application 231153 filed on Feb. 25, 2014, having the same title and inventor as the present application.

FIELD OF THE INVENTION

Various embodiments of the invention relate to baby accessories.

BACKGROUND OF THE INVENTION

Young babies often feel discomfort caused by gas in their digestive system. This phenomena, although rarely dangerous, causes enough pain or irritation to prevent the baby from sleeping and often results in prolonged crying.

Previously proposed solutions to gas pain in babies are described in U.S. Pat. No. 6,786,880; U.S. Pat. No. 5,423,875; U.S. Pat. No. 4,805,619; U.S. Pat. No. 4,397,315; U.S. Pat. No. 4,326,533; U.S. Pat. No. 3,175,558; U.S. Pat. No. 4,645,498; U.S. Pat. No. 3,889,684 and EP 0691111, each of which is fully incorporated herein by reference. This list does not purport to be exhaustive.

Several products for applying compresses are commercially available.

One product of this type is NEXCARE™ ColdHot Back & Abdomen Gel Pack Belt, by 3M. NEXCARE is a reusable gel compress that can be used hot or cold, with an adjustable belt. The belt contains THINSULATE™ Insulation Fabric that helps to retain temperature for longer. Another product of this type is COMFORT WRAP lower back and tummy heat pack belt from Saje Products. COMFORT WRAP is a heating pack to be applied to the lower back to ease back pain or to the abdomen to find solace from stomach aches or cramps. Again, this list does not purport to be exhaustive.

SUMMARY OF THE EMBODIMENTS

In some exemplary embodiments of the invention there is provided a baby compress including: a strip sized to be wrapped around the abdomen of a baby;
a pocket on the strip adapted to hold a liquid-soaked wipe, wherein the pocket has: an inner wall facing the baby and comprising mesh adapted to allow the liquid to permeate there through; and a back wall lined with impervious retention layer, adapted to reduce evaporation and leakage of the liquid through the back wall of the pocket; and a fastener for fastening said strip while it is wrapped around the abdomen of a baby. In some embodiments the baby compress further comprising a cover having an opening, wherein said cover is sized to fit into said pocket, and said wipe is sized to fit into said cover. Alternatively or additionally, in some embodiments the liquid comprises alcohol. Alternatively or additionally, in some embodiments the liquid comprises fragrance. Alternatively or additionally, in some embodiments the fragrance comprises aromatic oil. Alternatively or additionally, in some embodiments the liquid comprises medication. Alternatively or additionally, in some embodiments the fastener comprises VELCRO™ hooks. Alternatively or additionally, in some embodiments the strip is made of cloth. Alternatively or additionally, in some embodiments the strip is between 35 and 80 cm in length. Alternatively or additionally, in some embodiments the width of the strip is between 10 and 25 cm. Alternatively or additionally, in some embodiments the pocket includes a liquid absorbing layer. Alternatively or additionally, in some embodiments the liquid absorbing layer is made of cotton wool. Alternatively or additionally, in some embodiments the strip is made of elastic material, such as silicon. Alternatively or additionally, in some embodiments the inner layer comprises an insulation layer. Alternatively or additionally, in some embodiments the baby compress includes a wipe sized for insertion in the pocket. Alternatively or additionally, in some embodiments the wipe is a pre-soaked disposable wipe. Alternatively or additionally, in some embodiments the pre-soaked disposable wipe is supplied in a sealed package.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting. Unless marked as background or art, any information disclosed herein may be viewed as being part of the current invention or its embodiments.

BRIEF DESCRIPTION OF THE OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 2:
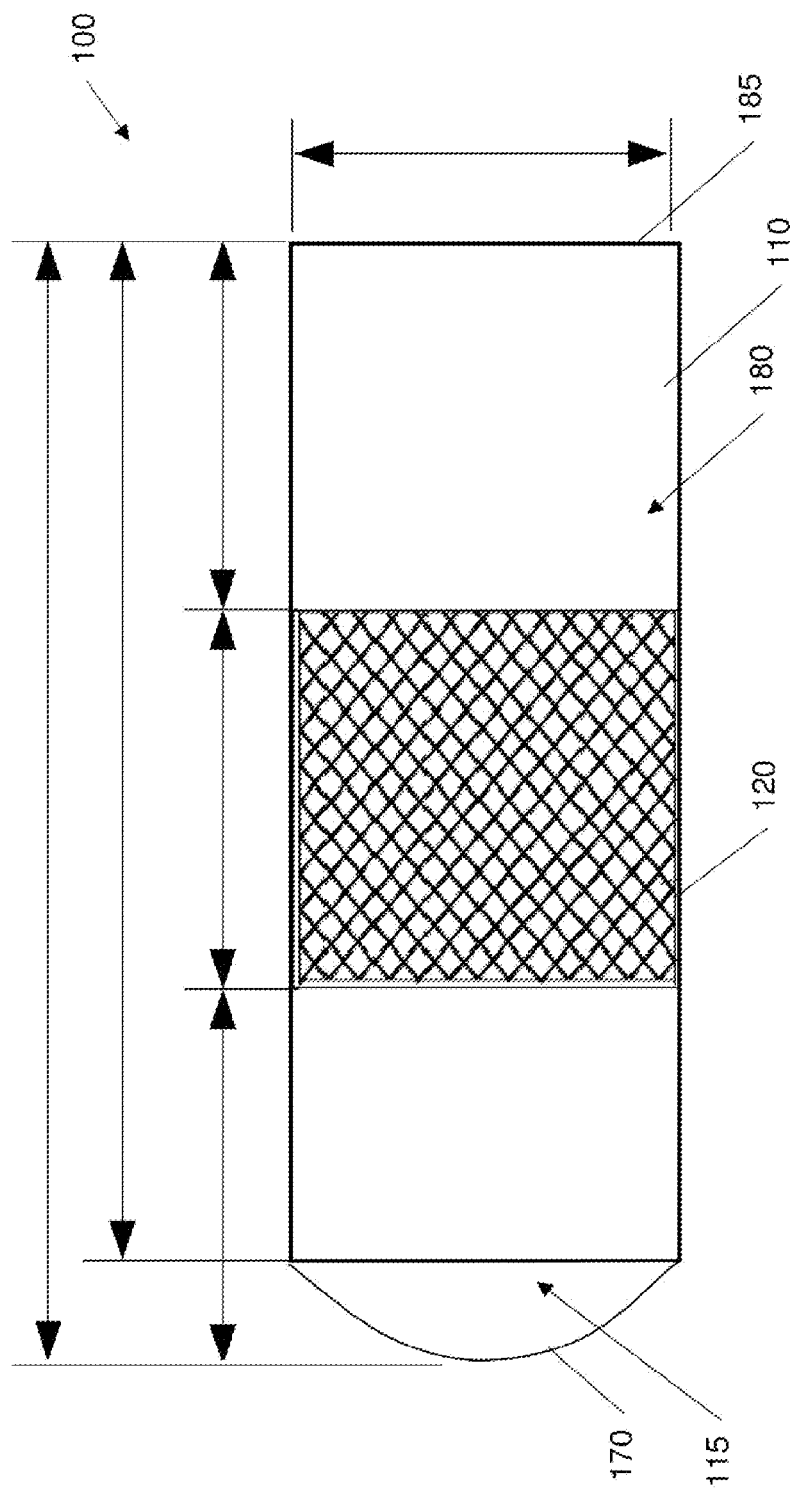
Figure 3:
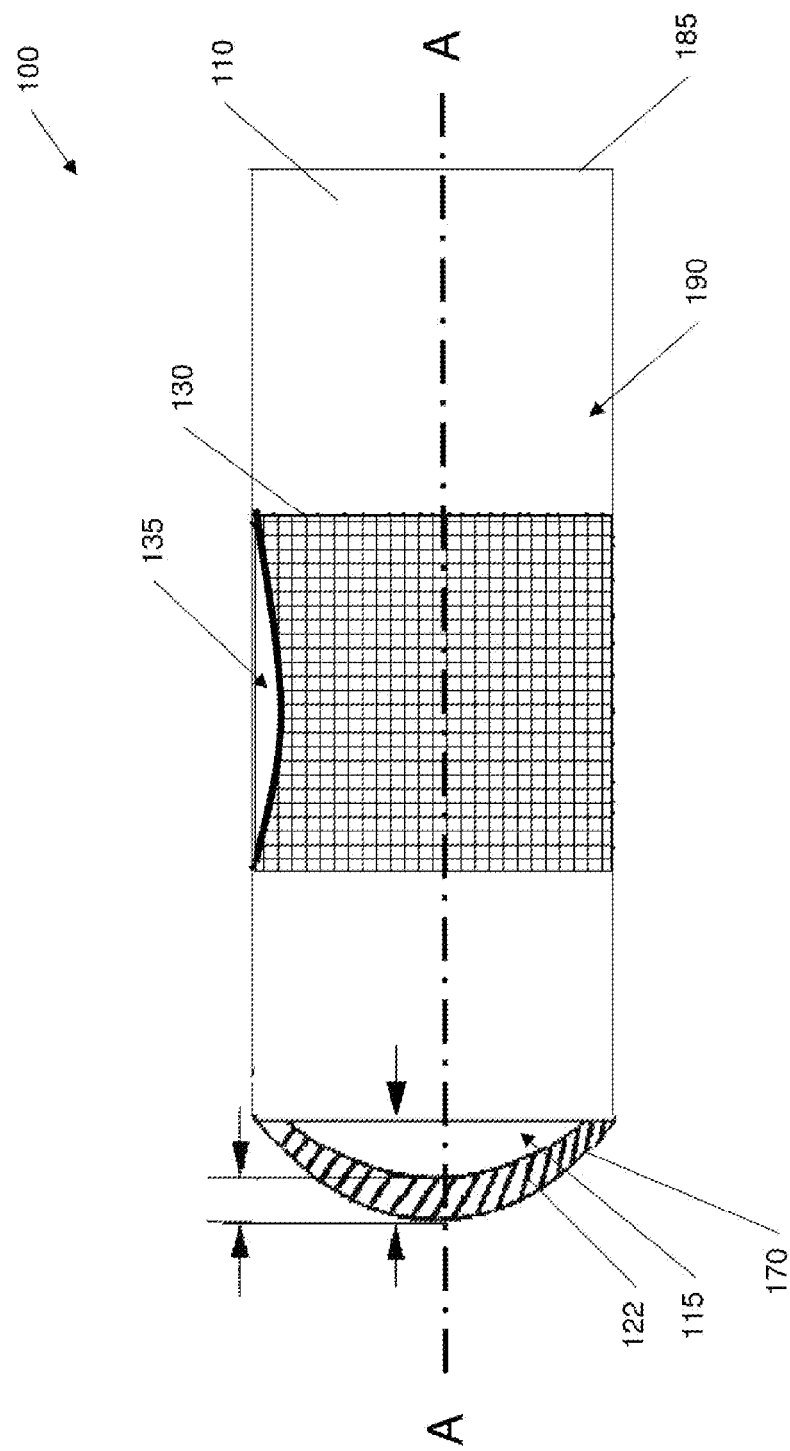
Figure 4:
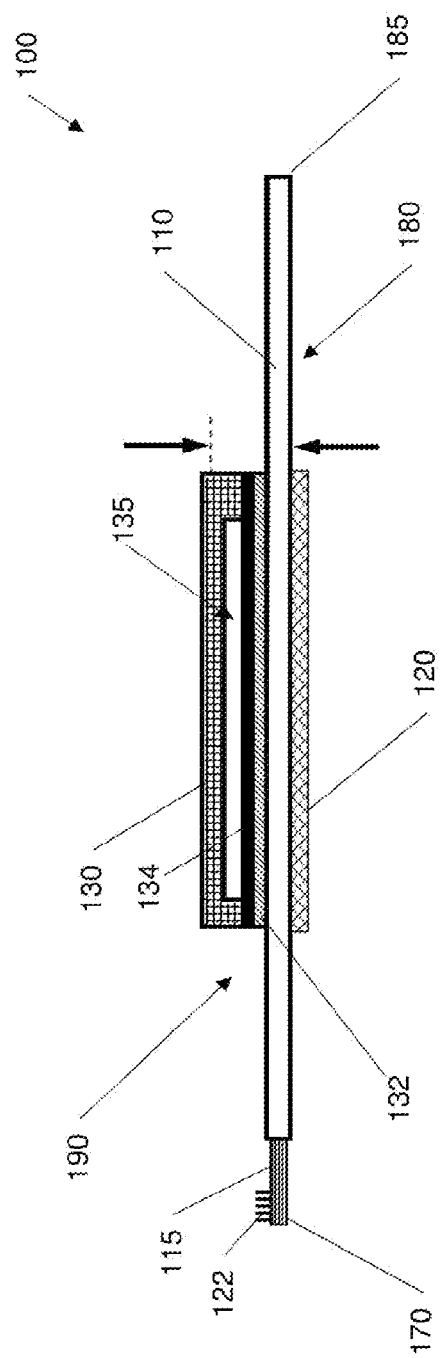
Figure 5:
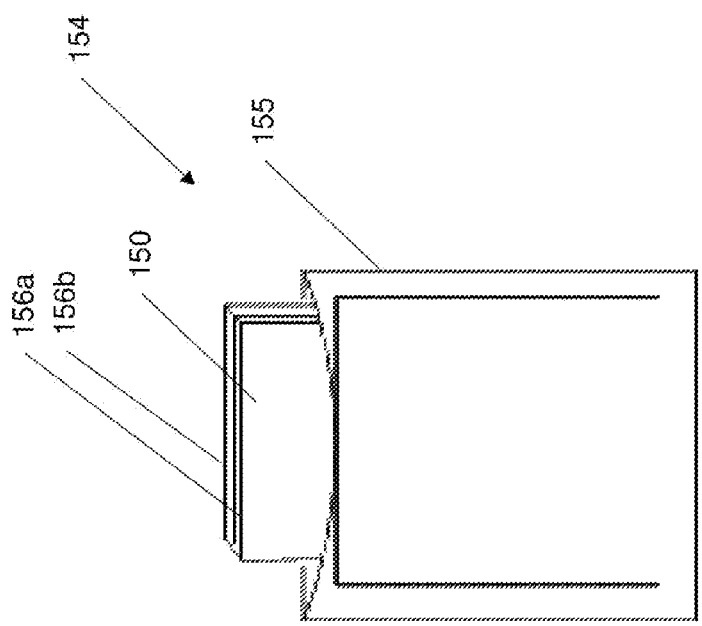
Figure 6:
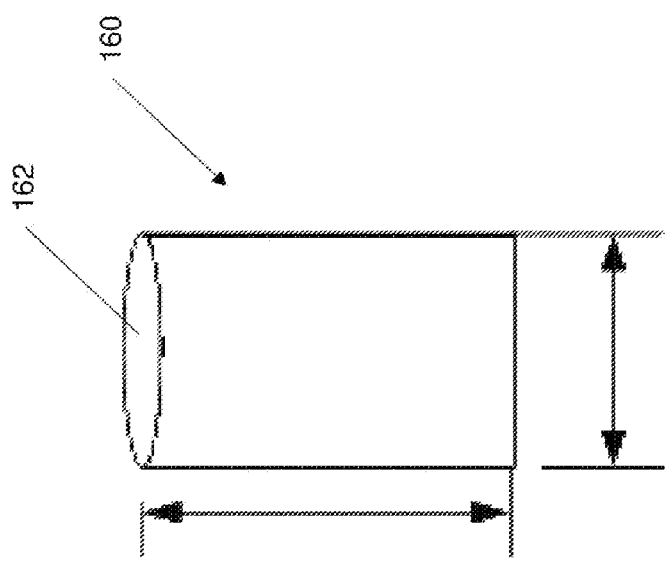

In the drawings:

FIG. 1 schematically illustrates a three dimensional isometric view of the baby compress according to an exemplary embodiment of the current invention;

FIG. 2 schematically illustrates a front view of the baby compress according to an exemplary embodiment of the current invention;

FIG. 3 schematically illustrates a back view of the baby compress according to an exemplary embodiment of the current invention;

FIG. 4 schematically illustrates a cross sectional view of the baby compress according to an exemplary embodiment of the current invention along the A-A line seen in FIG. 3;

FIG. 5 schematically illustrates a packaged of a wipe to be used with the baby compress according to an exemplary embodiment of the current invention; and FIG. 6 schematically illustrates a cover for a wipe to be used with the baby compress according to an exemplary embodiment of the current invention.

DETAILED DESCRIPTION OF EMBODIMENTS

Before explaining at least one embodiment of the invention in detail, it is to be understood that the invention is not necessarily limited in its application to the details set forth in the following description. The invention is capable of other embodiments or of being practiced or carried out in various ways.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

In discussion of the various figures described herein below, like numbers refer to like parts. The drawings are generally not to scale. For clarity, non-essential elements may have been omitted from some of the drawing.

Referring now to FIGS. 1 through 4: In accordance with exemplary embodiment of the current invention, a baby compress device indicated generally as 100 is provided. Device 100 comprises a cloth strip 110 sized to be wrapped around the abdomen of a human baby with some overlap. In some exemplary embodiments of the invention, strip 110 is approximately 60 cm long and 25 cm wide. The sizes and dimensions given here are purely exemplary and not limiting. In the depicted exemplary embodiment, a fastener including VELCRO Hooks™ 122 (FIGS. 3 and 4) located near the far end 170 on the inner side 190 of cloth strip 110 designed and configured to mate with and engage with a section of fluffy cloth or VELCRO™ loops 120 (FIGS. 1, 2 and 4) located on the outer side 180 of cloth strip 110 near its beginning end 185. In other embodiments, other fastener types are substituted for hooks 122 and loops 120. Other fastener types include, but are not limited to, adhesive strips, hooks, safety pins, buttons, laces, and snaps and zippers.

In an exemplary embodiment, an elastic section 115 is connected to the far end 170 of cloth strip 110 to provide elasticity. In some embodiments, elastic section 115 contributes to comfort of the baby as it breaths and/or moves around. Alternatively or additionally, other parts of device 100 are constructed of elastic material. In some exemplary embodiments of the invention, entire cloth strip 110 is made of elastic material. Examples of elastic material suited for use in various embodiments of the invention include silicone and rubber.

In the depicted embodiment, elastic section 115 is about 5 cm long, and the distal 2 cm of it are covered with VELCRO™ hooks 122. The mating section of fluffy cloth or VELCRO loops 120 is about 20 cm long. This configuration contributes to a capacity to accommodate a large range of baby sizes with the same baby compress 100. Alternatively or additionally, this configuration contributes to a capacity to accommodate a single baby as it grows over time. Alternatively or additionally, in some embodiments different sizes of baby compress 100 are available to be used with different sizes of baby such as: Extra Large (XL), Large (L), Medium (M) and Small (S). In some embodiments, each size is adjustable to fit a range of body sizes as described above.

In the depicted exemplary embodiment, the center of device 100 includes a pocket 135 into which a wipe 150 (FIG. 1) is inserted. In the depicted exemplary embodiment, wipe 150 is inserted into cover 160 which is then inserted in pocket 135. In some embodiments, wipe 150 is a piece of absorbent paper or a towel soaked with liquid. According to various exemplary embodiments of the invention the liquid in which wipe 150 is soaked includes one or more of alcohol, fragrance, aromatic oils or medications. According to various exemplary embodiments of the invention the liquid in which wipe 150 is soaked is formulated to soothe the baby when applied to the abdomen. Specifically, the liquid may be formulated to relieve or reduce pain and/or discomfort caused by gas in the baby's digestive system.

Referring now to FIG. 5, in some embodiments, wipe 150 is supplied pre-soaked in a liquid tight package. Alternatively or additionally, in some embodiments wipe 150 is a disposable wipe for single use and is discarded and replaced. In other exemplary embodiments of the invention, wipe 150 is designed and constructed to be re-used by soaking it with fresh liquid before each use. In Reusable embodiments of wipe 150, the material of which wipe 150 can be designed to pass through multiple laundry cycles in a household washing machine without significant degradation.

In some embodiments, device 100 is designed and configured for multiple use cycles and can be placed on a baby and be removed from the baby by fastening and unfastening fastener 122/120 repeatedly. In other exemplary embodiments of the invention, device 100 is provided as a single-use product to be disposed of after use. Configuration as a single use product contributes to a reduction in manufacturing cost and/or sale price. In single use embodiments, low cost materials such as paper and adhesive tape can be substituted for cloth in strip 110 and fastener 122/120 respectively.

In the depicted embodiment, pocket 135 is approximately 20 cm long and about as wide as cloth strip 110. The wall of pocket 135 close to the baby (on the inner side 190 of compress 100) is made of a thin porous cloth or mesh 130 which allows the liquid in wipe 150 seep through and contact the baby. Alternatively or additionally, in some embodiments the back side of pocket 135 is lined with retention layer 134 (FIG. 1). In some embodiments, retention layer 134 is made of Nylon™ or other plastic material. In some embodiments, retention layer 134 contributes to a reduction in evaporation of liquid from wipe 150 and/or leakage through outer side 180 of compress 100.

In the depicted exemplary embodiment, between retention layer 134 and inner side 190 of baby compress 100, there an insulation layer 132. In some embodiments, insulation layer 132 is made of cotton wool. Insulation layer 132 contributes to an increase in temperature of wipe 150 in pocket 135. In some embodiments, an increase in temperature of wipe 150 contributes to efficiency of release of the liquid of wipe 150. In some embodiments, increased efficiency of liquid release prolongs the length of time that device 150 remains effective. In some embodiments, insulation layer 132 has a thickness of 0.5 cm.

FIG. 5 schematically illustrates a packaged wipe indicated generally as 154 to be used with baby compress 100 according to an exemplary embodiment of the invention.

In FIG. 5 packaged wipe 154 is seen with packaging (depicted as envelope 155) opened. The packaging is made of liquid proof material such as plastic and is sealed with a pre-soaked wipe 150 inside it. In the depicted embodiment wipe 150 is made of two layers of liquid absorbing sheets 156a and 156b. In other exemplary embodiments of the invention, greater or lesser numbers of layers are employed. In some embodiments, wipe 150 is made of a single folded sheet.

FIG. 6 schematically illustrates a cover 160 for a wipe to be used with the baby compress 100 according to an exemplary embodiment of the current invention.

Cover 160 is preferably made of liquid absorbing cloth in a form of a pocket, sleeve or a sock having an opening 162 at one end. In operation, wipe 150 is inserted into cover 160 via opening 162 to produce a loaded cover which is then inserted into pocket 135 of compress 100 (as indicated in FIG. 1). Cover 160 prevents direct contact of wipe 150 with the skin of the treated baby. Alternatively or additionally, cover 160 contributes to distribution of the liquid in wipe 150 over the surface of the skin of the baby.

In some embodiments, cover 160 is sized to accommodate wipe 150 and/or fit within pocket 135 of compress 100. For example, cover 160 may be 8 cm wide by 14 cm tall; however other sizes may be used.

In some modes of use, cover 160 is immersed in lukewarm or slightly heated water before wipe 150 is inserted into it, or after wipe 150 is inserted but before it is inserted into pocket 135 of the baby compress 100. According to these modes of use, warm water contributes to the soothing effect. Alternatively or additionally, the warm water contributes to an increase in the evaporation of alcohol in wipe 150. Alternatively or additionally, the warm water contributes to increased absorption of liquid from wipe 10 into the skin of the baby.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method for relieving abdominal gas in a baby's digestive system, the method comprising:
   placing a liquid-soaked wipe in a pocket affixed to a strip sized to be wrapped around the abdomen of a baby as a compress, where a liquid of the liquid soaked wipe is formulated to relieve or reduce pain and/or discomfort caused by gas in the baby's digestive system, said compress comprising:
   a strip;
   said pocket on said strip adapted to hold said liquid-soaked wipe, wherein said pocket has an inner wall facing the baby and having mesh adapted to allow the liquid to permeate therethrough; and
   a back wall lined with impervious retention layer, adapted to reduce evaporation and leakage of the liquid through the back wall of the pocket; and
   a fastener;
   wrapping the strip around the abdomen of the baby, with the inner wall of the pocket facing the baby; and
   fastening said strip while it is wrapped around the abdomen of the baby with said fastener.

2. The method of claim 1 wherein said liquid further comprises one or more of medication, alcohol, and fragrance.

3. The method of claim 2 wherein said fragrance comprises an aromatic oil.

4. The method of claim 1 wherein said fastener further comprises one of adhesive strips, hook and loops, safety pins, buttons, laces, snaps, or zippers.

5. The method of claim 1 wherein the strip is made of cloth.

6. The method of claim 5 wherein said cloth further comprises an elastic material.

7. The method of claim 6 wherein said elastic material is rubber or silicone.

8. The method of claim 1 wherein said back wall further comprises an insulation layer.

9. The method of claim 1 wherein said insulation layer is made of cotton wool.

10. The method of claim 1 wherein said liquid-soaked wipe is a disposable wipe.

11. The method of claim 10 wherein said disposable wipe is supplied in a sealed package.

12. The method of claim 1 further comprising reusing said liquid-soaked wipe in a future application by soaking said liquid-soaked wipe with fresh liquid before each use.

* * * * *